United States Patent [19]

Bousseau et al.

[11] Patent Number: 5,624,945

[45] Date of Patent: Apr. 29, 1997

[54] USE OF RILUZOLE FOR THE TREATMENT OF NEURO-AIDS

[75] Inventors: Anne Bousseau; Adam Doble, both of Paris; Erik Louvel, Manosque, all of France

[73] Assignee: Rhone-Poulenc Rorer S.A., Antony, France

[21] Appl. No.: 396,106

[22] Filed: Feb. 28, 1995

Related U.S. Application Data

[63] Continuation of Ser. No. 109,559, Aug. 20, 1993, abandoned.

[30] Foreign Application Priority Data

Mar. 5, 1993 [FR] France .................... 93 02568

[51] Int. Cl.$^6$ .............................................. A61K 31/425
[52] U.S. Cl. .............................................. 514/367
[58] Field of Search ...................................... 514/367

[56] References Cited

U.S. PATENT DOCUMENTS

| | | | |
|---|---|---|---|
| 4,370,338 | 1/1983 | Mizoule | 424/270 |
| 4,826,860 | 5/1989 | Johnson et al. | 514/367 |
| 4,918,090 | 4/1990 | Johnson et al. | 514/367 |

FOREIGN PATENT DOCUMENTS

| | | | |
|---|---|---|---|
| 0282971 | 9/1988 | European Pat. Off. . | |
| 7308499 | 3/1973 | Japan | A01N 9/12 |
| 48-8499 | 3/1977 | Japan . | |

OTHER PUBLICATIONS

A. Falkenbach et al., "Abnormalities in Cholesterol Metabolism Cause Peripheral Neuropathy and Dementia in AIDS—A Hypothesis", Medical Hypotheses, 33:57–61 (1990).
B. Navia et al., "The AIDS Dementia Complex: I. Clinical Features", Annals of Neurology, 19(6):517–524 (1986).
B. Navia et al., "The AIDS Dementia Complex: II. Neuropathology", Annals of Neurology, 19(6):525–535 (1986).
Atwood, Human Immunodeficiency Virus Type I Infection of the Brain, Clin. Microbiol. Rev. vol. 6, No. 4, pp. 339–366 (1993).
Portegies, Declining Incidence of Aids dementia complex after introduction of zidovudine treatment, BMJ vol. 299, pp. 819–821 (1989).
Lipton, Calcium Channel antagonists and HIV Coat Protein–medicated Neuronal Injury, Annals of Neurology, vol. 30, pp. 110–114 (1991).
Levi, HIV coat protein gp 120 inhibits the β-adrenergic regulation of astroglial and microglial functions, Proc. Natl. Acad. Sci., USA, vol. 90, pp. 1541–1545 (1993).
Sundar, HIV glyoprotein gp 120) infused into rat brain induces interleukin 1 to elevate pituitary–adrenal activity and decrease peripheral cellular immune responses, Proc. Natl. Acad. Sci., USA, vol. 88, pp. 11246–11250.
WHO Classification of Dementia, p. 148. No date.
Genis, Cytokines and Arachidonic Metabolites Produced during HIV–infected Macrophase–Astroglia Interactions: Implications for the Neuropathogenesis of HIV Disease, J. Experim. Med., vol. 176, pp. 1703–1718 (1992).
Debono, Inhibition by riluzole of electrophysiological responses mediated by rat kainate and NMDA receptors expressed in Xenopus oocytes, Eur. J. Pharm. vol. 235, pp. 283–289 (1993).
Lipton, Synergistic Effects of HIV Coat Protein and NMDA Receptor–Mediated Neurotoxicity, Neurotoxicity, Neuron, vol. 7, pp. 111–118 (1991).
Darnell et al., Molecular Cell Biology, Scientific American Books, 1985 Ed., pp. 208–217.
Steadman's Medical Dictionary, 26th ed., p. 1945. No Date.
WHO International Statistical Classification of Diseases and Related Health Problems, ICD–10 (1992).
Lipton, Models of neuronal injury in AIDS: another role for the NMDA Receptor, TINS, vol. 15, No. 3, pp. 75–79 (1992).
Dreyer, HIV–1 Coat Protein Neurotoxicity Prevented by Calcium Channel Antagonists, Science, vol. 248, pp. 364–367 (1990).
American Psychiatric Classification of Dementia, Diagnostic Criteria from DSM–11, pp. 88–91. No Date.
Annual Meeting of the American Epilepsy Society, Dec., vol. 33, Suppl. 3, p. 69 (1992) Koppel et al., "Antiepileptic Drug Treatment in Patients with AIDS".
Arch. Neurol. vol. 48, No. 12, 1991, pp. 1281–1284, Kieburtz et al. "Excitotoxicity and dopaminergic dysfunction in the Acquired Immunodeficiency Syndrome Dementia Complex".
J. Neurosci, Nov. 1989, vol. 9, No. 11 pp. 3720–3727, "Malgouris C et al" Riluzole, a novel antiglutamate, prevents memory loss and hippocampal neuroal damage in ischemic gerbils.
Curr. Opin. Neurol. Neurosurg. vol. 5, No. 4, 1992, pp. 508–513; B.S. Meldrum et al. "Excitatory amino acid receptors and disease."
Rapport de Recherche, dated Aug. 4, 1993.

Primary Examiner—Russell Travers
Attorney, Agent, or Firm—Finnegan, Henderson, Farabow, Garrett & Dunner, L.L.P.

[57] ABSTRACT

The invention relates to the application of riluzole or the pharmaceutically acceptable salts of this compound in the treatment of neuro-AIDS.

10 Claims, No Drawings

USE OF RILUZOLE FOR THE TREATMENT OF NEURO-AIDS

This is a continuation of application Ser. No. 08/109,559, now abandoned, filed on Aug. 20, 1993.

The present invention relates to a novel therapeutic application of riluzole or the pharmaceutically acceptable salts of this compound.

Riluzole or the pharmaceutically acceptable salts of this compound are described as anticonvulsants and antiepileptics, in particular in Patent EP 50,551.

It has now been found, surprisingly, that this compound may also be used in the treatment of neuro-AIDS.

The term neuro-AIDS includes disorders involving dementia, cognitive disorders, neuropathies myopathies, ocular disorders and all neurological symptoms associated with the HIV-1 virus.

The activity of riluzole in neuro-AIDS was demonstrated in the test of neuronal death induced by the gp120 protein, an envelope protein of the HIV-1 virus, according to the following protocol:

Cortical cell cultures are prepared according to the method described by SINDOU et al, Brain Res., 572, 242–246 (1992). After 8 to 10 days of culture, neurons which have acquired a correct neural shape are used for the tests. The cells are kept at 37° C. in a $CO_2$ incubator for the whole of the experiment.

Neuronal survival is assessed before application and after 24 hours of application of the test product by a colorimetric technique using Tuspan Blue, counting predetermined fields (semi-quantitative method). A minimum of 4 culture dishes per concentration (100 neurons per dish) were analysed.

In a first series, neuronal survival in the culture medium was determined without any product. Neuronal survival is then approximately 87%.

In a second series, the toxicity of the gp120 in culture was demonstrated. The gp120 was applied alone to the culture medium for 24 hours at a concentration of 20 pM, and brings about a neuronal death which is of the order of 43%.

In the third series, the test product dissolved in dimethyl sulphoxide ($10^{-3}$M) is applied 5 minutes before the application of gp120 and thereafter incubated for 24 hours at concentrations from $10^{-7}$ to $10^{-8}$M. The results obtained are as follows:

| SERIES 1 CONTROLS NEURONAL SURVIVAL | SERIES 2 NEURONAL SURVIVAL gp120 alone (20 pM) | SERIES 3 NEURONAL SURVIVAL gp120 and riluzole ($10^{-7}$ M) |
| --- | --- | --- |
| 87.2 ± 7.2% | 57.3 ± 9.1% | 80.6 ± 9.9% |

As pharmaceutically acceptable salts, there may be mentioned, in particular, the addition salts with inorganic acids, such as hydrochloride, sulphate, nitrate or phosphate, or organic acids, such as acetate or propionate, succinate, oxalate, benzoate, fumarate, maleate, methanesulphonate, isethionate, theophyllineacetate, salicylate, phenolphthalinate, methylenebis(β-hydroxynaphthoate) or substitution derivatives of these compounds.

The medicinal products consist at least of riluzole, in free form or in the form of an addition salt with a pharmaceutically acceptable acid, in the pure state or in the form of a composition in which it is combined with any other pharmaceutically compatible product, which may be inert or physiologically active. The medicinal products according to the invention may be employed orally or parenterally.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica, under a stream of argon. These compositions can also contain substances other than diluents, for example one or more lubricants such as magnesium stearate or talc, a colorant, a coating (dragées) or a varnish.

As liquid compositions for oral administration, pharmaceutically acceptable solutions, suspensions, emulsions, syrups and elixirs, containing inert diluents such as water, ethanol, glycerol, vegetable oils or liquid paraffin, may be used. These compositions can comprise substances other than diluents, for example wetting, sweetening, thickening, flavouring or stabilizing products.

The sterile compositions for parenteral administration can preferably be suspensions, emulsions or aqueous or non-aqueous solutions. As a solvent or vehicle, water, propylene glycol, a polyethylene glycol, vegetable oils, especially olive oil, injectable organic esters, for example ethyl oleate, or other suitable organic solvents may be employed. These compositions can also contain adjuvants, especially wetting agents, tonicity agents, emulsifiers, dispersants and stabilizing agents. The sterilization may be carried out in several ways, for example by aseptic filtration, by incorporating sterilizing agents in the composition, by irradiation or by heating. They may also be prepared in the form of sterile solid compositions which can be dissolved at the time of use in sterile water or any other sterile injectable medium.

The doses depend on the effect sought, the treatment period and the administration route used; they are generally between 50 and 400 mg per day orally for an adult, with single doses ranging from 25 to 200 mg of active substance.

Generally speaking, the doctor will determine the appropriate dosage in accordance with the age and weight and all other factors distinctive to the subject who is to be treated.

The examples which follow illustrate medicinal products according to the invention:

Example A

Tablets containing a 50 mg dose of active product and having the following composition are prepared according to the usual technique:

| | |
| --- | --- |
| Riluzole | 50 mg |
| Mannitol | 64 mg |
| Microcrystalline cellulose | 50 mg |
| Povidone excipient | 12 mg |
| Carboxymethylstarch sodium | 16 mg |
| Talc | 4 mg |

-continued

|  |  |
|---|---|
| Magnesium stearate | 2 mg |
| Colloidal silica, anhydrous | 2 mg |
| Mixture of methylhydroxypropylcellulose, polyethylene glycol 6000 and titanium dioxide (72:3.5:24.5) | |
| q.s. 1 finished film-coated tablet weighing | 245 mg |

Example B

Hard gelatin capsules containing a 50 mg dose of active product and having the following composition are prepared according to the usual technique:

|  |  |
|---|---|
| Riluzole | 50 mg |
| Cellulose | 18 mg |
| Lactose | 55 mg |
| Colloidal silica | 1 mg |
| Carboxymethylstarch sodium | 10 mg |
| Talc | 10 mg |
| Magnesium stearate | 1 mg |

Example C

An injectable solution containing 10 mg of active product and having the following composition is prepared:

|  |  |
|---|---|
| Riluzole | 10 mg |
| Benzoic acid | 80 mg |
| Benzyl alcohol | 0.06 cm$^3$ |
| Sodium benzoate | 80 mg |
| Ethanol, 95% | 0.4 cm$^3$ |
| Sodium hydroxide | 24 mg |
| Propylene glycol | 1.6 cm$^3$ |
| Water q.s. | 4 cm$^3$ |

The invention also relates to the process for preparing medicinal products which are useful in the treatment of neuro-AIDS, consisting in mixing riluzole or the pharmaceutically acceptable salts of this compound with one or more compatible and pharmaceutically acceptable diluents and/or adjuvants.

We claim:

1. Method for the treatment of neuro-AIDs which comprises administering to a patient in recognized need of such treatment an effective amount of Riluzole or a pharmaceutically acceptable salt thereof.

2. Method for the treatment of neuro-AIDs induced by the gp120 protein which comprises administering to a patient in recognized need of such treatment an effective amount of Riluzole or a pharmaceutically acceptable salt thereof.

3. Method for the treatment of neuro-AIDS dementia, neuro-AIDS cognitive disorders, neuro-AIDS neuropathies, neuro-AIDS myopathy, or ocular neuro-AIDS disorders which comprises administering to a patient in recognized need of such treatment an effective amount of Riluzole or a pharmaceutically acceptable salt thereof.

4. Method for increasing neuronal survival in the presence of the HIV-1 virus which comprising administering to a subject in need of such treatment an effective amount of riluzole or a pharmaceutically acceptable salt thereof.

5. Method for increasing neuronal survival in a human patient in the presence of gp 120 protein, comprising administering to the patient an effective amount of riluzole or a physiologically acceptable salt thereof.

6. Method according to claim 5 for the treatment of neuro-AIDS dementia, neuro-AIDS cognitive disorders, neuro-AIDS neuropathies, neuro-AIDS myopathy, or neuro-AIDS ocular disorders associated with the gp 120 protein.

7. Method for reducing neuronal death induced by gp 120 protein in a human patient comprising, administering to the patient an effective amount of riluzole or a physiologically acceptable salt thereof.

8. Method according to claim 7 for the treatment of neuro-AIDS dementia, neuro-AIDS cognitive disorders, neuro-AIDS neuropathies, neuro-AIDS myopathy, or neuro-AIDS ocular disorders associated with the gp 120 protein.

9. Method according to claim 5 for the treatment of a neurological symptom associated with the gp 120 protein.

10. Method according to claim 7 for the treatment of a neurological symptom associated with the gp 120 protein.

* * * * *

UNITED STATES PATENT AND TRADEMARK OFFICE
CERTIFICATE OF CORRECTION

PATENT NO. : 5,624,945            Page 1 of 2
DATED : April 29, 1997
INVENTOR(S) : Anne BOUSSEAU et al.

It is certified that error appears in the above-indentified patent and that said Letters Patent is hereby corrected as shown below:

Claim 1, column 4, line 2, "neuro-AIDs" should read --neuro-AIDS--.

Claim 1, column 4, line 4, "Riluzole" should read --riluzole--.

Claim 2, column 4, line 6, "neuro-AIDs" should read --neuro-AIDS--.

Claim 2, column 4, line 9, "Riluzole" should read --riluzole--.

Claim 3, column 4, line 14, "Riluzole" should read --riluzole--.

UNITED STATES PATENT AND TRADEMARK OFFICE
CERTIFICATE OF CORRECTION

PATENT NO. : 5,624,945
DATED : April 29, 1997
INVENTOR(S) : Anne BOUSSEAU, et al It is certified that error appears in the above-identified patent and that said Letters Patent is hereby corrected as shown below:

Claim 3, column 4, line 14, "Riluzole" should read --riluzole--.

Signed and Sealed this

Ninth Day of December, 1997

*Attest:*

BRUCE LEHMAN

*Attesting Officer*     Commissioner of Patents and Trademarks